(12) United States Patent
Okumoto

(10) Patent No.: US 6,173,716 B1
(45) Date of Patent: Jan. 16, 2001

(54) METHOD AND APPARATUS FOR INSPECTING CIGARETTE DENSITY

(75) Inventor: Yutaka Okumoto, Tokyo (JP)

(73) Assignee: Japan Tobacco, Inc., Tokyo (JP)

( * ) Notice: Under 35 U.S.C. 154(b), the term of this patent shall be extended for 0 days.

(21) Appl. No.: 09/047,417

(22) Filed: Mar. 25, 1998

(30) Foreign Application Priority Data

Mar. 25, 1997 (JP) .................................................. 9-071984

(51) Int. Cl.$^7$ ..................................................... A24C 5/18
(52) U.S. Cl. ..................... 131/84.1; 131/905; 131/907; 131/908; 131/910; 131/906
(58) Field of Search ..................... 131/905, 906, 131/907, 908, 910

(56) References Cited

U.S. PATENT DOCUMENTS

| 2,937,280 | 5/1960 | Gilman ................................ 250/83.3 |
| 2,954,775 | 10/1960 | Radley et al. ......................... 131/21 |
| 3,056,026 | 9/1962 | Bigelow .............................. 250/83.3 |
| 3,604,429 | * 9/1971 | De Witt .............................. 131/905 |
| 3,648,035 | * 3/1972 | Hart et al. ........................... 131/905 |
| 3,742,795 | * 7/1973 | Lipcon et al. ......................... 131/905 |
| 3,878,982 | * 4/1975 | Hoffman .............................. 131/905 |
| 4,249,544 | * 2/1981 | Reuland et al. ........................ 131/905 |
| 4,805,641 | * 2/1989 | Radzio et al. ......................... 131/905 |
| 4,865,054 | * 9/1989 | Lorenzen et al. ...................... 131/905 |
| 5,526,827 | * 6/1996 | Kubo et al. ........................... 131/906 |
| 5,967,148 | * 10/1999 | Harris et al. ......................... 131/905 |

FOREIGN PATENT DOCUMENTS 82288    1/1996  (JP) .

* cited by examiner

Primary Examiner—Stanley S. Silverman
Assistant Examiner—Michael P. Colaianni

(57) ABSTRACT

A density inspection apparatus and method. The apparatus is disposed downstream of a wrapping section of a cigarette manufacturing machine. In accordance with pulse output signals generated by a rotary encoder in synchronism with the travel of a cigarette rod, a zone of the rod is subjected to density inspection. An actual density signal indicating the tobacco shred filling density in the inspected zone is intermittently supplied from a density detector, and a group of reference density signals indicative of a change in density of a low-density portion of a dummy cigarette is supplied from a storage device. A difference between each actual density signal and a corresponding reference density signal is calculated, and the square sum of the signal differences in respect of all the density signals is calculated to determine a nonconformity degree between the actual and reference density signals. If the nonconformity degree of any one of the zones of the cigarette rod portion is small, this rod portion is determined as having a high possibility of including a local low-density portion.

16 Claims, 8 Drawing Sheets

METHOD AND APPARATUS FOR INSPECTING CIGARETTE DENSITY

BACKGROUND OF THE INVENTION

1. Technical Field

The present invention relates to a method and apparatus for inspecting the density of cigarettes, and more particularly, to a cigarette density inspection method and apparatus for detecting a local low-density portion of cigarettes.

2. Related Art

The quality of cigarettes may be impaired, if the filling density of tobacco shred in cigarettes (hereinafter, referred to as cigarette density) is nonuniform. For instance, if a cigarette includes a local low-density portion which expedites the burning of tobacco shreds, the flavor of smoking is degraded since an amount of air sucked by a smoker changes at the low-density portion.

One of the causes of the presence of a local low-density portion in cigarettes resides in that so-called puff tobacco leaves expanded by a treatment using carbon dioxide gas or the like are frequently used for the production of cigarettes. Tobacco shreds including puff tobacco are liable to be nonuniformly formed into a cigarette, so that nonuniformity occurs in the cigarette density. Another cause is that recent cigarette manufacturing machines are configured to wrap tobacco shreds by a paper web at a faster speed. The high wrapping speed makes it difficult to uniformly form cigarettes.

In the cigarette manufacturing process, cigarettes including a local low-density portion longer than a predetermined length are generally rejected as being faulty products. To this end, a density detector is mounted on a cigarette manufacturing machine, and, in accordance with the density signal generated by the density detector, inspection is made to determine whether a tobacco rod continuously produced by the cigarette manufacturing machine includes such a local low-density portion.

As disclosed in U.S. Pat. Nos. 2,954,775, 2,937,280, 3,056,026 and Japanese patent publication no. 8-2288, various density detectors are known, which utilize a relationship between cigarette density and penetration of beta radiation, X-ray radiation, infrared radiation or ultrasonic wave or between cigarette density and permittivity. Among these detectors, a beta radiation type density detector is mainly employed for the reason that it is largely unaffected by moisture content, tobacco-shred size and color of measured cigarettes, and is hence excellent in measurement stability, as compared to other types of density detectors.

Even in the case of using a radiation type density detector, however, a difficulty is encountered if an attempt is made to further improve the measurement accuracy. To accurately detect a local low-density portion in cigarettes, it is advisable to narrow the width of a window which is formed in a detecting section of the density detector and through which beta radiation passes. For instance, the window width may be narrowed to a value equivalent to the minimum length (e.g., 3–4 mm) of those local low-density portions which may cause the quality of cigarettes to be lowered to an extent that they are rejected as being faulty products.

If, however, the window width is narrowed to such an extent, the quantity of beta radiation passing through the window becomes smaller, lowering the measurement reliability. That is, the quantity of beta radiation generated by strontium-90, which is radioactive isotope and which collapses randomly, varies to form a binominal distribution, so that the standard deviation of a density signal obtained by measuring the quantity of beta radiation passing through the window is inversely proportional to the square root of the quantity of beta radiation passing through the window. In other words, the smaller the quantity of beta radiation becomes, the lower the reliability of density signal will be.

In order to simply increase the quantity of beta radiation passing through the window of a radiation type density detector, it is sufficient to use a detector which contains a larger amount of strontium-90. In this case, however, an amount of leakage of braking radiation increases.

If the quantity of beta radiation is small, the gain of an amplifier which constitutes part of a density detector must be increased, and a drift in the amplifier output is liable to increase. In this case, the density signal may be affected by the drift of the amplifier output, causing an error in the measurement, based on the density signal, of average cigarette weight which is important factor for management of cigarette quality.

To attach the importance to the accuracy of average cigarette weight measurement, the window width is usually set to a value equivalent to cigarette diameter, e.g., about 8 mm, as disclosed in U.S. Pat. 3,056,026, although it is apparent that the accuracy of detection of a low-density cigarette portion can be improved by using a density detector which is narrow in window width.

However, it is difficult to detect a local low-density portion on the basis of the output from a radiation type density detector which is so configured to generate the output suitable to measure the average cigarette weight. More specifically, if a density detector, having the window width equivalent to the cigarette diameter, is used to detect a local low-density portion which is approximately 3–4 mm in length and which has a weight about 65–70% lighter than that of a standard density portion, the waveform of the density signal is distorted because of the window width which is longer than the length of the local low-density portion. That is, even if the low-density portion, having a density which is discontinuous from that of a standard-density portion, passes the window of the density detector, the density signal merely changes in a manner describing a gentle valley. In addition, a change in density signal level observed between when the standard-density portion passes the detector and when the low-density portion passes the same is about half of the density difference between these two portions. Namely, only 20% drop occurs in signal level even for a low-density portion whose density is 40% smaller than that of the standard-density portion.

A variation (standard deviation) in weight in the axial direction of a cigarette having 8 mm diameter is generally in the order of 8%. Thus, a variation of about ±24% may occur in an ordinary signal level, if the window width is widened, attaching to the importance to the accuracy of average weight detection, up to a value of 8 mm which is about three times larger than the length (approximately 3 mm) of local low-density portion to be detected. Thus, a change in signal level in the order of 20% indicative of the presence of local low-density portion cannot be distinguished from the ordinary variation of about 24% in signal level.

As a consequence, it is difficult to appropriately carry out both the measurement of average cigarette weight and the detection of local low-density portion, based on the density signal obtained by a radiation type density detector formed with a window which is large in width. This is also true of to density detectors of types other than the radiation type.

SUMMARY OF THE INVENTION

An object of the present invention is to provide a method and apparatus for cigarette density inspection for easily and reliably detecting a local low-density portion in cigarettes.

The present inventor noted that the waveform of a density signal, supplied from a density detector provided with a window which is wider than a local low-density portion of a cigarette and observed when such a portion passes the detector, is distorted in a manner proper to the detector in accordance with the shape of the window and the response characteristic of the detector. The present inventor realized that a signal component indicative of such a local low-density portion can be extracted from a density signal, even if the detector has such a wide window as to generate a density signal suitable to the measurement of average cigarette weight. Based on this recognition, a method and apparatus of the present invention for inspecting a cigarette density have been created.

According to one aspect of the present invention, a cigarette density inspection method is provided, which comprises the steps of: (a) detecting in advance, as a reference density signal, a density signal indicating a density of a reference cigarette which includes a local low-density portion; (b) detecting, as an actual density signal, a density signal which indicates a density of an inspected cigarette; (c) determining a correlation between a changing pattern of the reference density signal and that of the actual density signal: and (d) determining whether the inspected cigarette includes a local low-density portion based on the correlation determined in said step (c).

According to another aspect of the present invention, there is provided a cigarette density inspection apparatus for a cigarette manufacturing machine having a wrapping section for wrapping tobacco shreds by a paper web to thereby obtain a continuous cigarette rod which includes cigarette rod portions respectively corresponding to individual cigarette products into which the cigarette rod is cut. The density inspection apparatus comprises: a density detector disposed on a side downstream of the wrapping section, for generating a density signal indicating a density of the cigarette rod passing the density detector; a storage device for storing in advance a reference density signal indicating a density of a reference cigarette which includes a local low-density portion; a nonconformity degree determining section for determining a nonconformity degree between a changing pattern of the reference density signal which is determined based on the reference density signal stored in the storage device and a changing pattern of an actual density signal which is determined based on the density signal generated by said density detector when the cigarette rod passes the density detector; and a low-density determining section for determining that the cigarette rod includes a local low-density portion if the nonconformity degree is less than an allowable limit.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Figure 1:
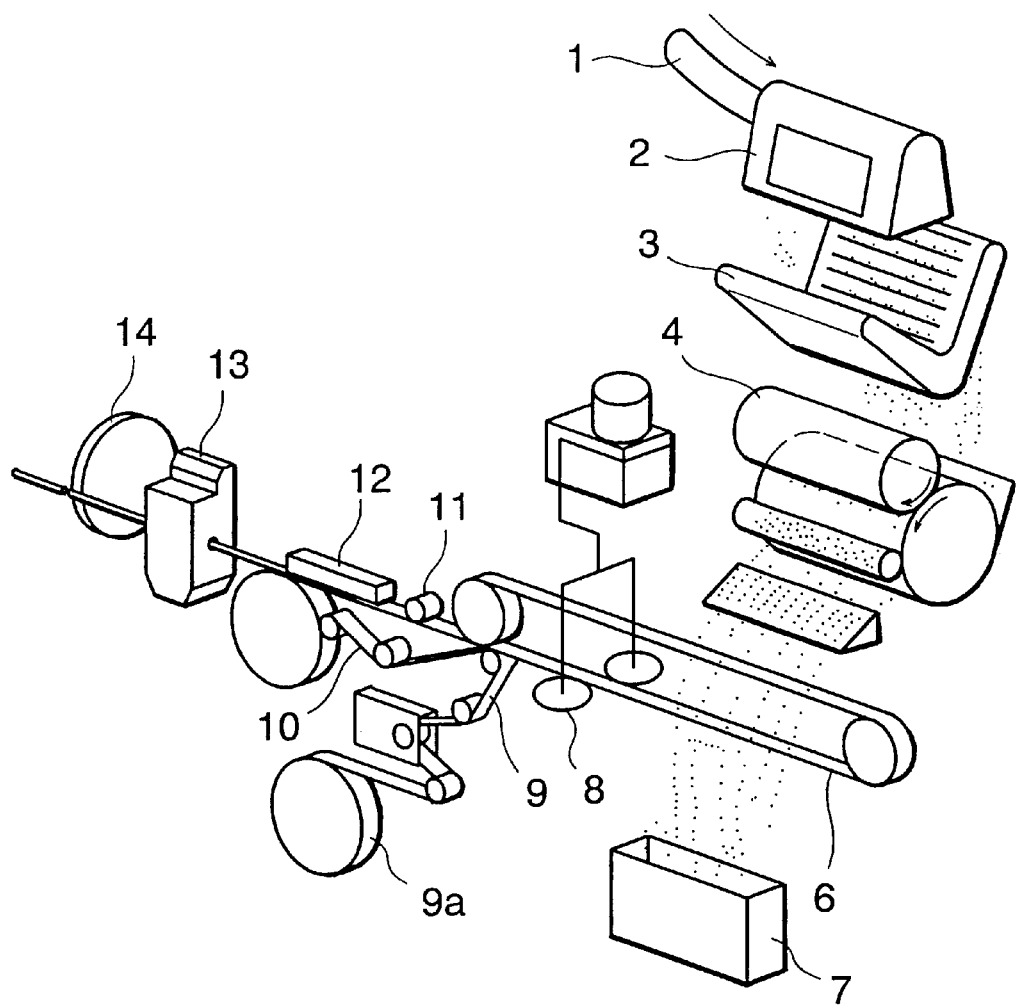
FIG. 1 is a schematic perspective view of a typical cigarette manufacturing machine.

A density inspection apparatus according to an embodiment of the present invention for detecting a local low-density portion of cigarettes will be explained with reference to the accompanied drawings.

First, referring to FIG. 1, a brief explanation as to cigarette manufacturing processes will be given. Tobacco shreds are transported by air, through a feed pipe 1 of a cigarette manufacturing machine, to a separator 2 where the tobacco shreds are separated from air and then drop onto a needle belt 3. The tobacco shreds are disentangled and conveyed upward by the needle belt 3, and drop of f an upper edge of the needle belt 3 onto a needle drum 4. With rotation of the needle drum 4, the tobacco shreds are discharged from the drum 4 at a constant rate toward the front of the machine. At this stage, the tobacco shreds which are light in weight are separated from foreign matters which are heavy in weight, such as sand. The tobacco shreds are conveyed by air, which flows through a perforated belt 6, to be attached by suction to the lower surface of the belt 6, whereas the foreign matters are discharged into a receiver box 7.

The perforated belt 6 to which the shredded tobacco is attached is traveled to the left in FIG. 1. During the transportation of the shredded tobacco by means of the belt 6, the thickness of the shredded tobacco attached in layer to the belt 6, i.e., the filling amount (density) of tobacco shreds in cigarette, is adjusted by a trimming device 8 disposed in a shredded-tobacco transportation path which is partly formed by the perforation belt 6.

The cigarette manufacturing machine includes a wrapping section in which the shredded tobacco is transferred from the perforation belt 6 onto a paper web 9 which is supplied from a reel 9a and which is traveled along the shredded-tobacco transportation path together with a garniture tape 10. In the wrapping section, the shredded tobacco is continuously wrapped by the paper web 9 into a cigarette rod. During this time, one longitudinal edge portion of the paper web 9 is supplied with paste by a paste roller 11 and is then overlapped and affixed to another edge portion of the paper web. The pasted portion of the cigarette rod is dried by a heater 12.

The cigarette rod thus manufactured is caused to pass through a radiation type density detector 13 disposed on the side downstream of the wrapping section, so that the density (filling amount of shredded tobacco) of the cigarette rod is measured and inspected. After passing the density detector 13, the cigarette rod is divided by a cutter blade 14 into individual cigarette products, each having a predetermined length. In other words, the cigarette rod includes cigarette rod portions corresponding to the individual cigarette products. If the result of inspection based on the output of the density detector 13a indicates that a cigarette product is low in average density or includes a local low-density portion, such a cigarette is rejected as being a faulty cigarette product.

Figure 2:
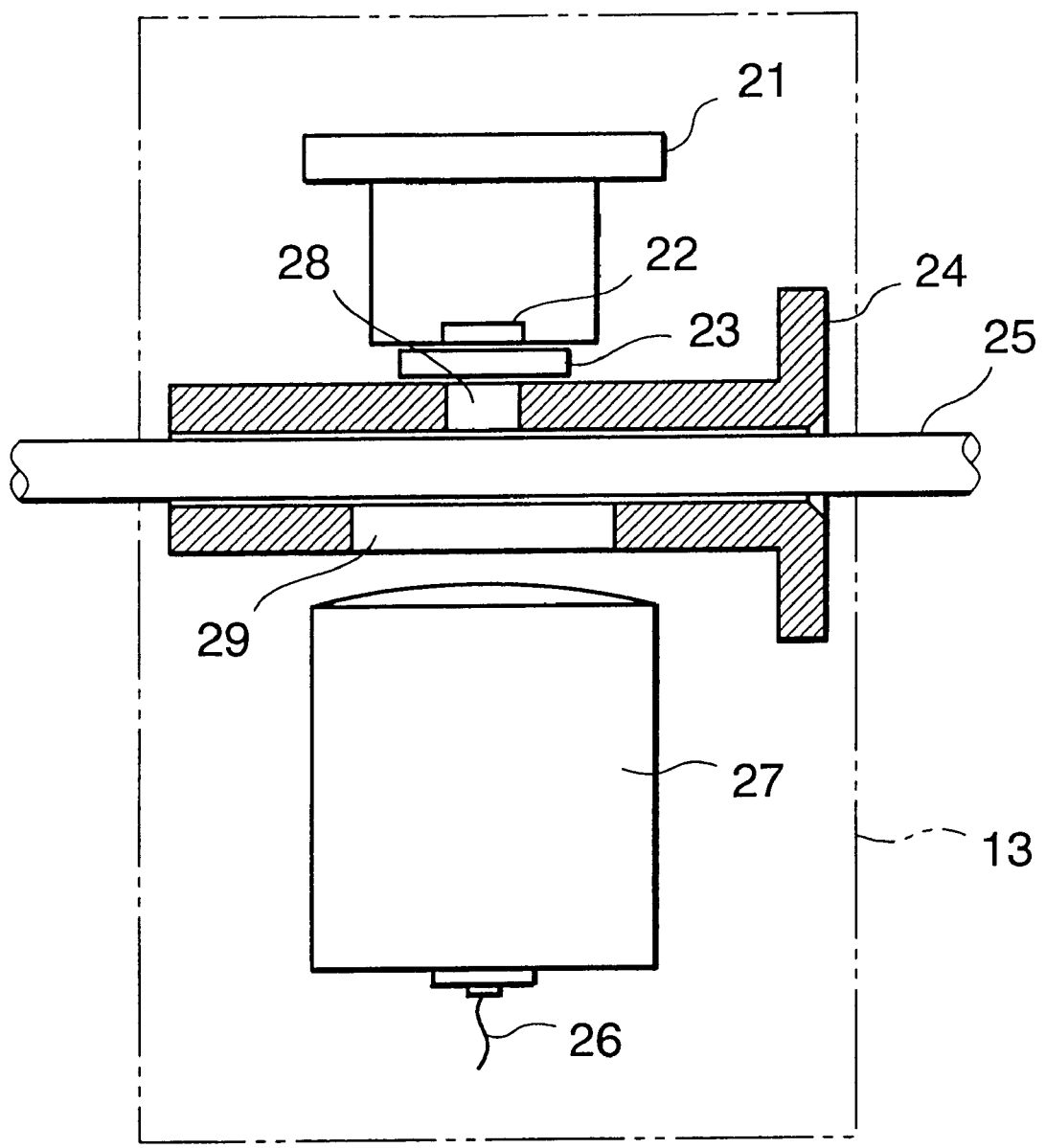
FIG. 2 is a view showing, partly in section, a radiation type density detector shown in FIG. 1.

The radiation type density detector 13 is configured as shown in FIG. 2. The density detector 13 has a container 21 which accommodates therein radioactive isotope 22, typically, strontium-90. When a shutter 23 of the container 21 is caused to open, the beta radiation generated by the radioactive isotope 22 passes through an irradiation window 28 formed in a cigarette holder pipe 24, so that the cigarette rod 25 is exposed to the beta radiation. After passing through the cigarette rod 25, the beta radiation passes through a detection window 29 and enters an ionization chamber 27. This chamber 26 is applied with a high voltage and is adapted to output an electric current at its signal line 26. Based on the electric current which varies in proportion to the quantity of beta radiation entering the ionization chamber 27, the density of the cigarette rod 25 is measured.

In this embodiment, the width of the irradiation window 28 and that of the detection window 29 are 8 mm and 16 mm, respectively, for a case where the cigarette rod 25 has its diameter of 8 mm.

Figure 3:
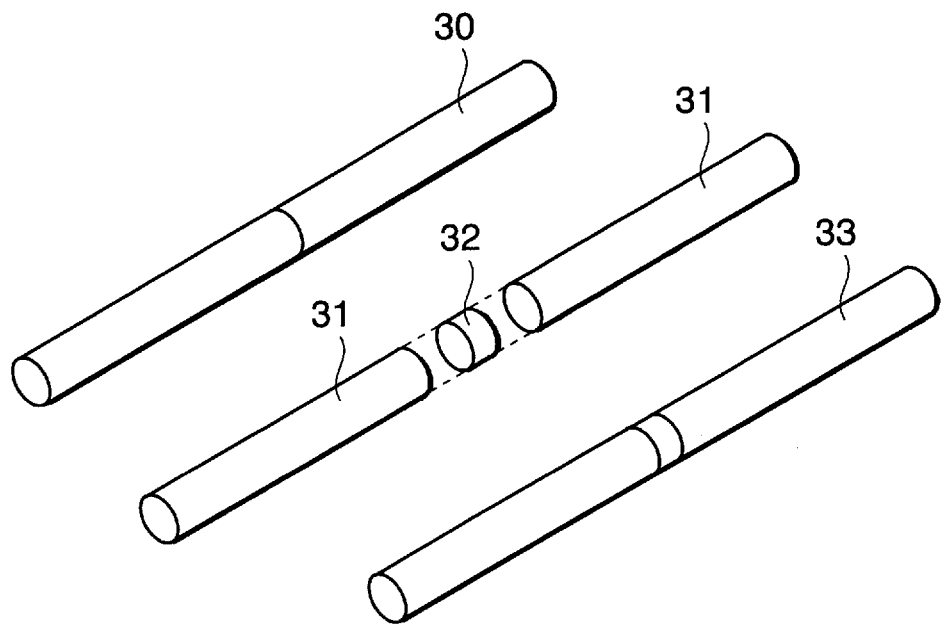
FIG. 3 is a perspective view showing a dummy cigarette which includes a local low-density portion.

In order to prepare reference data for the detection of a local low-density portion of cigarettes manufactured by the aforementioned cigarette manufacturing machine, a dummy cigarette (reference cigarette or faulty cigarette) is produced which includes a local low-density portion. As shown in FIG. 3, the dummy cigarette 33 is obtained by bonding a short cigarette portion 32 to long cigarette portions 31 at their opposite end faces or by wrapping these portions 32 and 31 by a thin paper, with the short portion 32 interposed between the long portions 31. The short cigarette portion 32, serving as a model of local low-density portion, has a length and density which are respectively equal to a minimum length and maximum density of those local low-density portions which are to be rejected. For instance, the short cigarette portion 32 has a length of 3 to 4 mm and a density corresponding to 60 to 75% of a standard density. The long cigarette portions 31 are obtained by dividing a cigarette 30, having the standard density, into two pieces.

Figure 4:
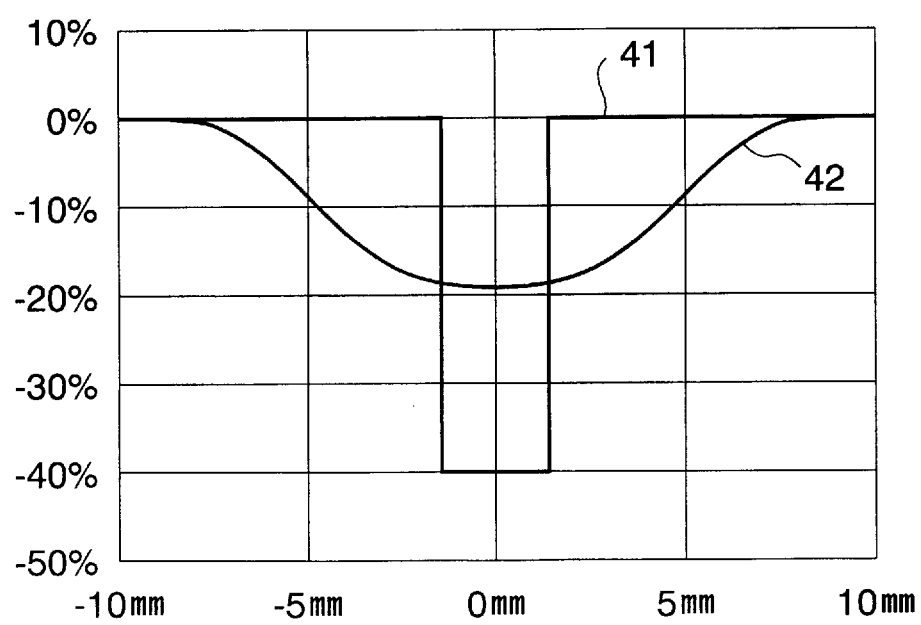
FIG. 4 is a graph showing a relationship between an actual tobacco shred filling density of the dummy cigarette shown in FIG. 3 and the waveform of the density signal observed when the local low-density portion and its adjacent portions of the dummy cigarette passes through the density detector shown in FIG. 2.

FIG. 4 shows a waveform of a density signal generated by the radiation type density detector 13 when the local low-density portion and adjacent portions of the dummy cigarette 33 pass through the detector 13. Despite that the actual density around the local low-density portion of the dummy cigarette 33 varies in the form of a rectangular pulse as shown by characteristic line 41, the waveform of the output signal of the density detector 13 (changing pattern of reference density signal) continuously varies to describe a gentle valley around a signal portion corresponding to the local low-density cigarette portion, as shown by characteristic line 42. In other words, the output signal of the density detector 13 is distorted as compared to the actual density distribution.

This waveform distortion is caused by the shape and size (wider than the local low-density portion 32) of the window 28 of the radiation type density detector 13, the response speed of the detector 13 and the like, and indicates a distortion which is proper to the density detector 13. Accordingly, if the output of the density detector 13 as shown by the characteristic line 42 is observed during the passage of a measured cigarette rod, then it can be considered that the actual shredded-tobacco filling density in the measured cigarette varies as shown by the characteristic line 41, so that the measured cigarette rod includes a local low-density portion.

Thus, in the present embodiment, a function g(t) indicative of the characteristic line 42 is stored in advance as a changing pattern of reference density signal. Then, a detection signal f(t), representative of a changing pattern of actual density signal, is obtained when the measured cigarette rod passes through the density detector 13, and a correlation between the function g(t) and the detection signal f(t) is determined. More specifically, in order to evaluate the extent to which the detection signal f(t) is in nonconformity with the function g(t), a nonconformity degree therebetween is determined in accordance with the following equation (1) or (2):

$$A=\int (f(t)-g(t))^2 dt \quad (1)$$

$$A=\int |f(t)-g(t)| dt \quad (2).$$

According to equation (1), the nonconformity degree is obtained as the square-sum of differences between the detection signal f(t) and the function g(t). Equation (2) calculates the total sum of the absolute values of the differences between these signals. The zone for which the arithmetic operation to calculate the sum is set to a value corresponding to the window width of the detector 13. If the nonconformity degree calculated is less than a predetermined nonconformity degree, then it can be determined that the density distribution in that zone of the measured cigarette rod which corresponds to the detection width is similar to the density distribution around the low-density portion of the dummy cigarette 33, so that the aforementioned cigarette rod zone can be determined as including a local low-density portion. Based on the timing at which such a low density is detected, the cigarette rod portion (cigarette product) which includes a local low-density portion can be specified.

Figure 5:
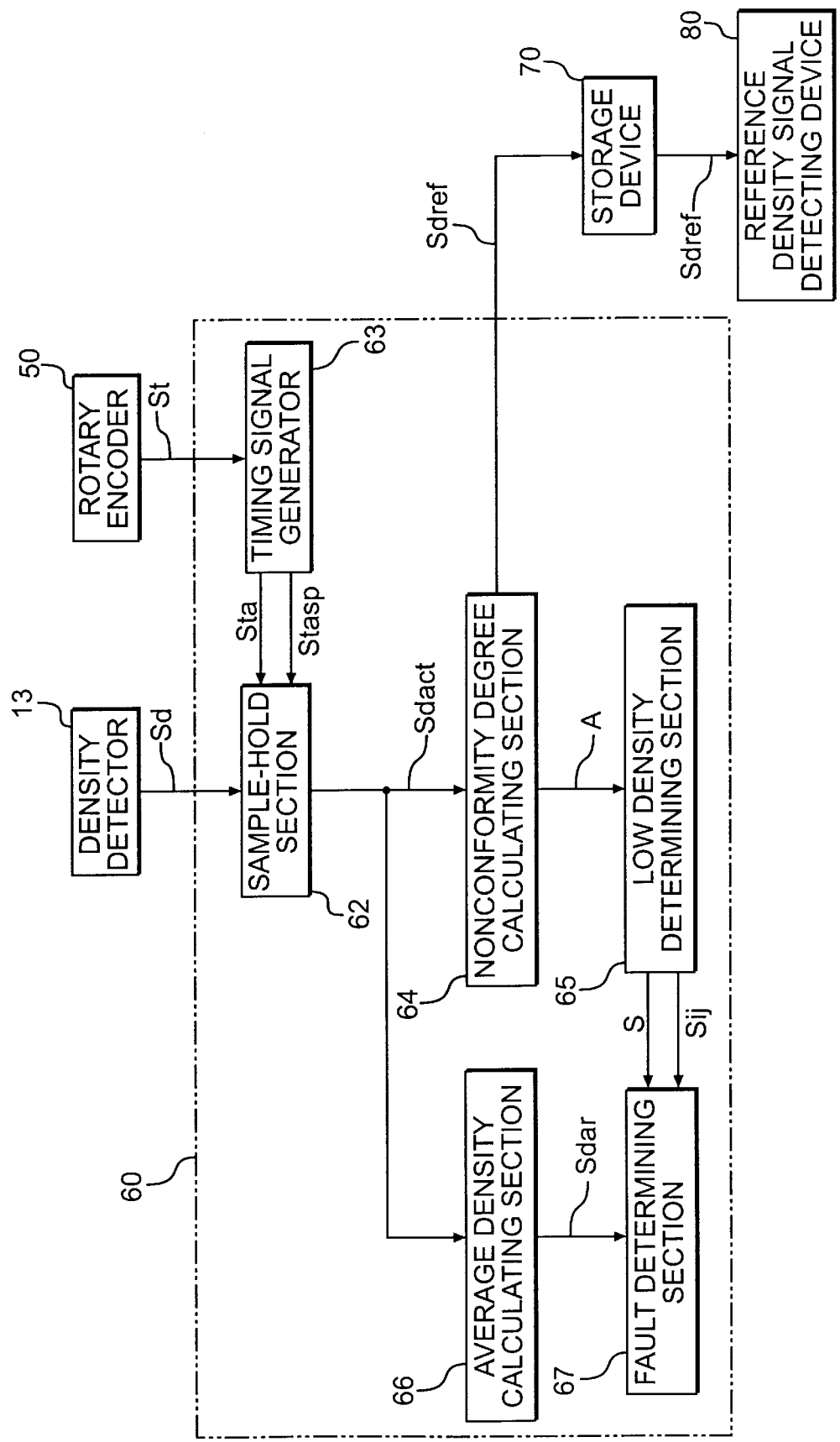
FIG. 5 is a schematic block diagram showing various functional sections of a computer which serves as a primary constituent of a density inspection apparatus according to an embodiment of the present invention.
Figure 5A:
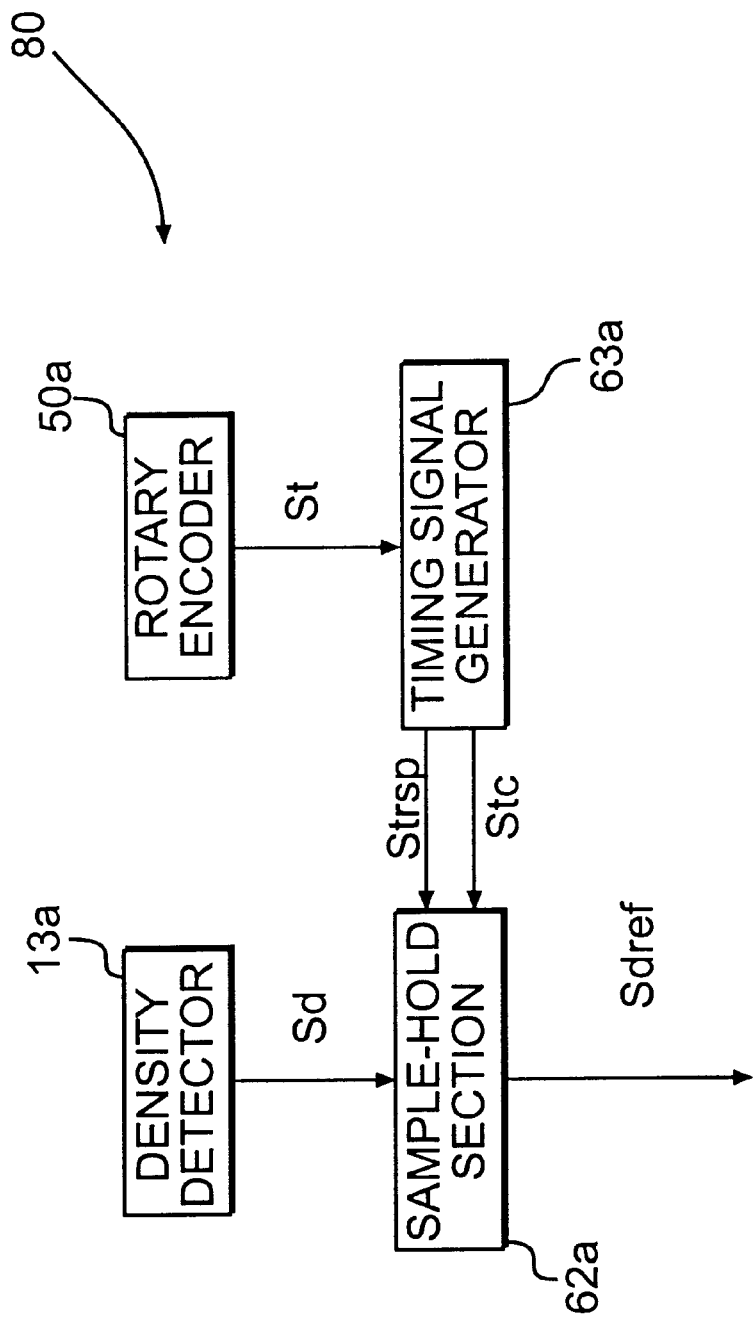
FIG. 5(a) is a schematic block diagram of the reference density signal detecting device.

The density inspection apparatus of this embodiment includes a computer 60 which has functions of various sections thereof shown in FIG. 5, and a storage device 70 for storing in advance a group of reference density signals Sdref (FIG. 6) which corresponds to the function g(t) shown in equation (1) or (2) and which represents the changing pattern of the reference density signal. The reference density signals Sdref are detected with use of, e.g., a reference-density-signal detecting device 80 which may be comprised of a sensor for detecting the opposite ends of the dummy cigarette 33, and elements (not shown) corresponding to the density detector 13, rotary encoder 50, sample-hold section 62 and timing signal generator 63 which are used for the detection of a group of actual density signals Sdact corresponding to the detected signal f(t) shown in equation (1) or (2) and representing the changing pattern of the actual density signal. In the following explanation, those elements of the detecting device 80 which correspond to the elements 13, 50, 62 and 63 shown in FIG. 1 are denoted by like numerals to which suffix "a" is attached. The density detector 13a of the detecting device 80 has the same characteristic as that of the density detector 13 shown in FIG. 1.

Instead of using the detecting device 80, the cigarette manufacturing machine may be so modified as to achieve the functions of the reference-density-signal detecting device 80. In this case, a sensor for detecting opposite ends of the dummy cigarette 33 may be provided in the cigarette manufacturing machine, if necessary.

Figure 6:
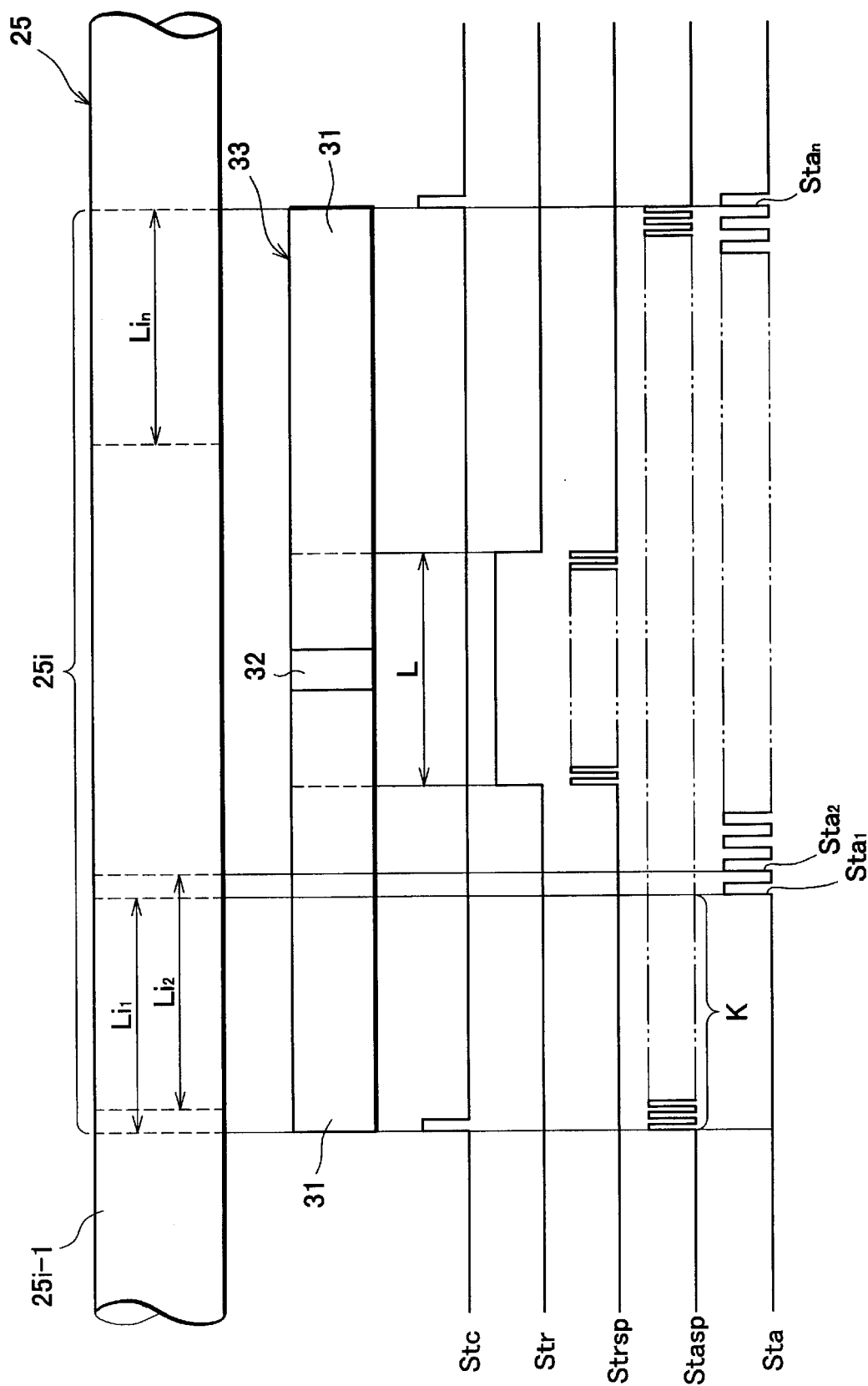
FIG. 6 is a graph showing timing at which actual and reference density signals are sampled.

As shown in FIG. 6, the reference-density-signal detecting device 80 is so configured as to sequentially deliver the reference density signals Sdref which are sampled at intervals of a predetermined period by the sample-hold section 62a as a predetermined cigarette zone L (FIG. 6) passes through the density detector 13a of the detecting device 80. The predetermined cigarette zone L includes the short cigarette portion (local low-density portion) 32 of the dummy cigarette 33 which corresponds to the width of the calculation section shown in FIG. 4.

More specifically, the timing signal generator 63a of the detecting device 80 counts the pulse outputs of the rotary encoder 50a which are generated in sequence just after the start end of the dummy cigarette 33 is detected, and determines time points at which the start and terminal ends of the predetermined cigarette zone L pass through the density detector 13a, respectively. Further, the timing signal generator 63a delivers a high-level zone signal Stc from when the start end of the zone L is detected to when the terminal end of the zone L is detected. Further, as the zone signal Stc is at the high level, the timing signal generator 63a generates a sampling command Strsp at intervals of a predetermined period. This sampling period is set to such a time interval as to permit retrieval of a suitable number K of density signals enough to appropriately detect a density signal changing pattern in the predetermined cigarette zone L. The sample-hold section 62a retrieves, as the reference density signal Sdref, the density signal Sd supplied from the density detector 13a each time it receives the sampling command Strsp. A group of the reference density signals Sdref thus sampled and indicating the changing pattern of the reference density signal is stored sequentially in the storage device 70.

In the density inspection of the cigarette rod, the computer 60 retrieves the density signal Sd from the density detector 13, as the actual density signal Sdact, at intervals of the same period as the sampling period of the reference density signal Sdref, in each of plural zones of each cigarette rod portion (corresponding to one cigarette product) of the cigarette rod to be inspected. In FIG. 6, the i-th (i=1, 2,—) cigarette rod portion 25i of the cigarette rod 25 is mainly illustrated. Symbol Lij represents the j-th zone (j=1, 2,—, n) of the i-th cigarette rod portion 25i. Each of the zones has the same length as that of the predetermined cigarette zone L of the dummy cigarette 33, and most part of each zone overlaps the next zone. Preferably, the length of non-overlapping zone between adjacent two zones is shorter than the minimum length (i.e., the length of the short cigarette portion of the dummy cigarette 33) of local low-density portions to be rejected.

In connection with the retrieval of the actual density signal Sdact, the computer includes a sample-hold section 62 for sampling, at intervals of a predetermined period, the density signal Sd continuously supplied from the density detector 13, and a timing signal generator 63 for receiving a pulse signal St generated, at a time interval corresponding to the traveling speed of the paper web, by a rotary encoder 50 attached to the rotating shaft of a drum (not shown) for driving the garniture tape.

More specifically, based on the pulse output signals St supplied from the rotary encoder 50, the timing signal generator 63 generates a cigarette start end signal Stc (corresponding to a cigarette-rod cutting command) each time it determines the start end of the i-th cigarette rod portion 25i, and generates sampling command Stasp at a time interval which is longer than the time interval at which the encoder output signal St is generated. In response to the i-th cigarette start end signal, the sample-hold section 62 terminates the retrieval of the actual density signal Sdact associated with the (i−1)-th cigarette rod portion 25i-1 and at the same time starts retrieval the actual density signal Sdact associated with the i-th cigarette rod portion 25i. The retrieving of the actual density signal Sdact is carried out in accordance with a sampling command Stasp supplied from the timing signal generator 63.

At the time when the retrieval of the actual density signal Sdact associated with the j-th zone Lij of the i-th cigarette rod portion 25i is completed, the timing signal generator 63 outputs an actual-density-signal output command Staj. In response to the output command Staj, the sample-hold section 62 transfers those actual density signals Sdact which correspond to the j-th zone Lij of the i-th cigarette rod portion 25i, among the sampled actual density signals Sdact, to a buffer memory (not shown) provided in the timing signal generator 63, and then causes a group of the actual density signals Sdact, corresponding to the j-th zone Lij, to be transferred in sequence from the buffer memory to a nonconformity degree calculating section 64 and to an average density calculating section 66.

The nonconformity degree calculating section 64 sequentially stores the group of the actual density signals Sdact, transferred from the sample-hold section 62 and representative of the changing pattern of the actual density signal, in a first buffer memory (not shown) of the calculating section 64, sequentially reads the group of the reference density signals Sdref from the storage device 61, and stores these signals Sdref in a second buffer memory (not shown). Next, the nonconformity degree calculating section 64 subtracts a corresponding one of the reference density signals Sdref from each actual density signal Sdact, thereby determining the defifference between these signals. The group of the actual density signals Sdact and the group of the reference density signals correspond to the detection signal f(t) and the function g(t) in equations (1) and (2), respectively. In accordance with equations (1) and (2), the square or the absolute value of the difference between each actual density signal Sdact and a corresponding reference density signal Sdref is determined, and further, as a nonconformity degree A, the square sum or the sum of the absolute values in respect of all the actual and reference density signals is determined.

A low-density determining section 65 of the computer 60 compares an allowable limit with the nonconformity degree A, determined by the nonconformity degree calculating section 64, in respect of the j-th zone Lij of the i-th cigarette rod portion 25i. If the result of this comparison indicates that the nonconformity degree A is less than the allowable limit, the determining section 65 determines that the changing pattern of the actual density signal is similar to that of the reference signal density, and supplies a fault determining section 67 with a low-density signal SL and a signal Sij which specifies the position of low-density portion.

An average density calculating section 66 adds up the actual density signals Sdact, sequentially transferred from the sample-hold section 62, in respect of the j-th zone Lij of the i-th cigarette rod portion 25i, to thereby calculate a total actual density signal value, and divides this total value by the number K of the actual density signals to thereby obtain an average density Sdav (FIG. 5) of the j-th zone Lij.

A fault determining section 67 determines whether the average density Sdav determined by the density calculating section 66 is less than an allowable density. If any one or more of plural zones Lil to Lim of the i-th cigarette rod portion 25i are determined to be low in density and if any one or more of the average densities of the determined one or more low-density zones are less than the allowable density, the fault determining section 67 determines that the cigarette rod portion 25i is faulty. The faulty cigarette rod portion is rejected by means of a conventional rejection device (not shown) after it is cut off from the cigarette rod 25.

In the following, the operation of the density inspection apparatus (i.e., a density inspection method) will be explained.

Figure 7:
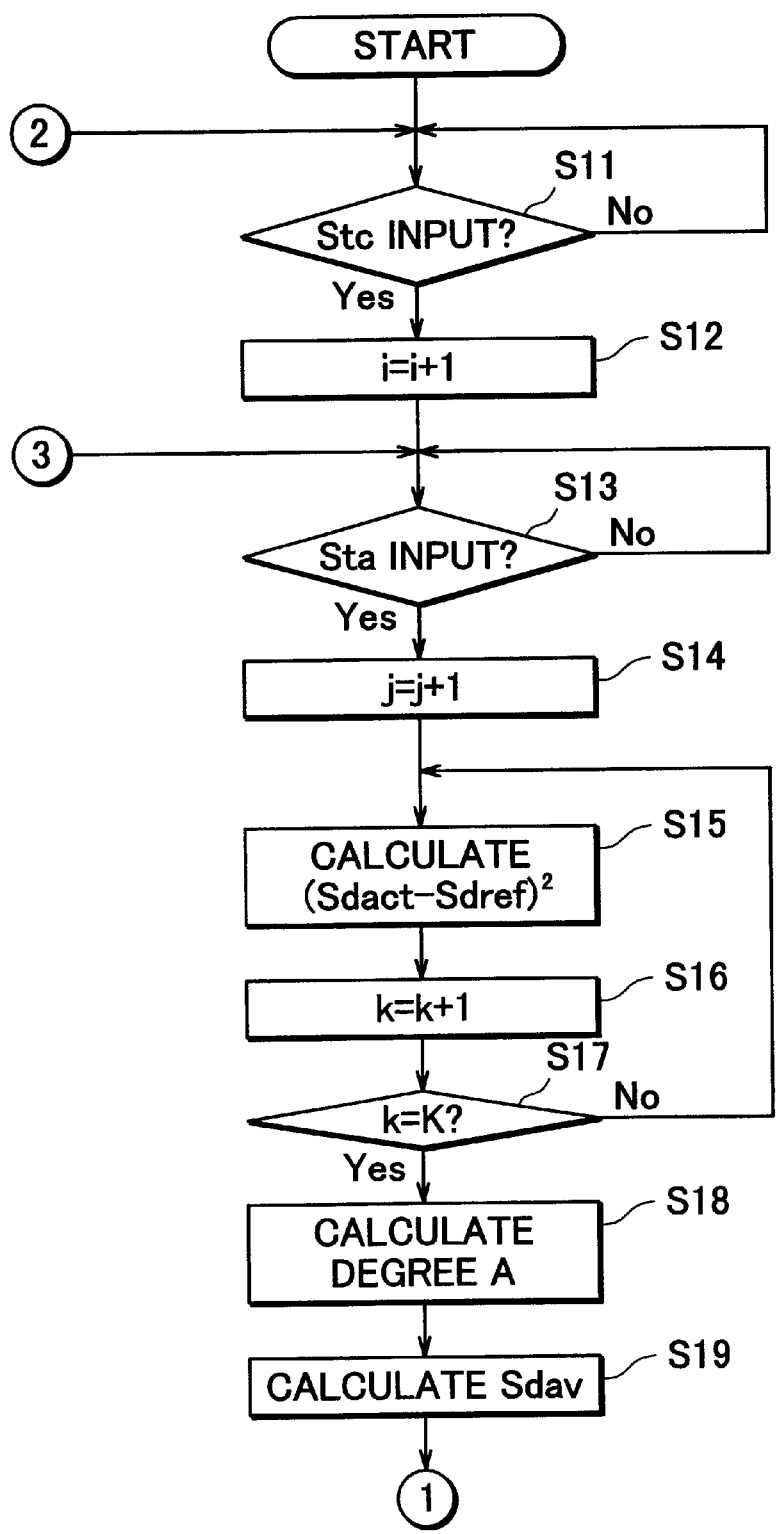
FIG. 7 is a flowchart showing part of a faulty cigarette determination routine executed by the computer shown in FIG. 5.
Figure 8:
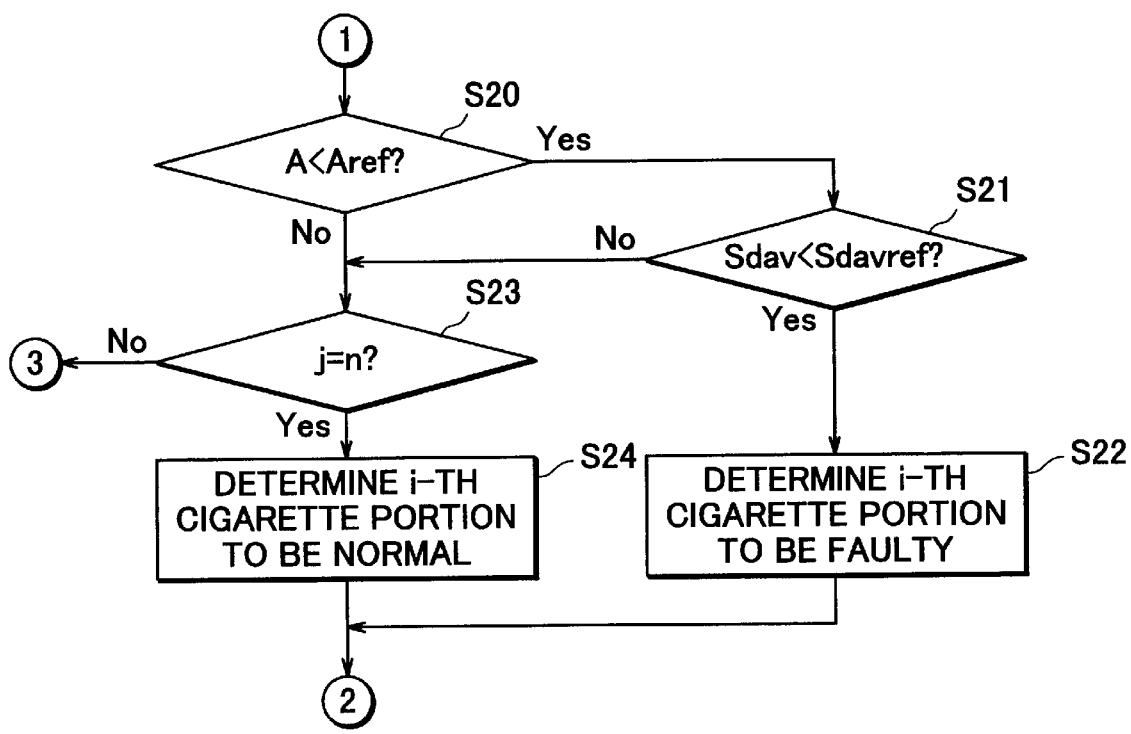
FIG. 8 is a flowchart showing the remaining part of the faulty cigarette determination routine.

During the operation of the cigarette manufacturing machine, the computer 60 of the density inspection apparatus executes a fault determination routine shown in FIGS. 7 and 8.

First, a determination is made at step S11 as to whether or not a cigarette-start-end signal Stc is generated. If the result of this determination is affirmative (Yes), a value of 1 is added to the present value of a parameter i (=1, 2,—), having an initial value equal to zero, which parameter specifies a cigarette rod portion, currently subjected to the density inspection, of the cigarette rod (step S12). Next, whether or not an actual-density-signal output command Sta is delivered is determined (step S13). If it is determined at step S13 that the command Sta is delivered, a value of 1 is added to the present value of a parameter j (=1, 2,—, n), having an initial value equal to zero, which specifies a zone, currently subjected to the inspection, of the cigarette rod portion having plural zones (step S14). If the j-th zone of the i-th cigarette rod portion is determined as being currently subjected to the density inspection, the nonconformity degree calculating section 64 reads a group of the actual density signals Sdact, which are associated with the j-th zone of the i-th cigarette rod portion 25i and which are K in number, from the sample-hold section 62 and stores the same in the first buffer memory of the calculating section 64. A group of the reference density signals Sdref, which are the same in number to the signals Sdact and associated with the j-th zone of the i-th cigarette rod portion, is read from the storage device 70 and is stored in the second buffer memory of the calculating section 64.

At step S15, the k-th actual density signal Sdact (k=1, 2,—, K) in respect of the j-th zone of the i-th cigarette rod portion is read from the first buffer memory, and the k-th reference density signal Sdref in respect of the same zone is read from the second buffer memory. Then, a calculation is made to determine the square of a difference between the actual and reference density signals, the difference being obtained by subtracting the reference density signal Sdref from the actual density signal Sdact (step S15). Next, a value of 1 is added to the present value of a parameter k (=1, 2,—, K), having an initial value equal to zero, which specifies a pair of the density signals subjected to the operation of calculating the square of the difference therebetween (step S16), and a determination is made as to whether or not the renewed parameter value k reaches the final value K (step S17). If it is determined at step S17 that the calculation of the square of the difference between the final actual density signal and the final reference density signal is completed, the squares of the density signal differences obtained by repeating, K times, the processes of step S15–S17 are added up in respect of K pairs of the actual and reference density signals, to thereby determine the nonconformity degree A between the changing patterns of the actual and reference density signals (step S18). The sum of the K actual density signals is divided by the signal number K, to thereby calculate an average density Sdav of the j-th zone of the i-th cigarette rod portion 25i (step S19).

Then, a determination is made as to whether or not the nonconformity degree A determined at step S18 is less than an allowable limit Aref (step S20). If the result of this determination is affirmative, whether or not the average density Sdav is less than an allowable density Sdavref is determined (step S21). If the result of the determination at step S21 is affirmative, the i-th cigarette rod portion 25i is determined to be fault (step S22). The control flow returns to step S11 where it awaits for the start of the density inspection in respect of the next cigarette rod portion.

In the density inspection for the j-th zone of the i-th cigarette rod portion 25i, if it is determined at step S20 that the nonconformity degree A between the changing patterns of the actual and reference density signals is not less than the allowable limit Aref and hence the density of the j-th zone of the i-th cigarette rod portion is sufficient, the control flow returns to step S13 where it awaits for the start of the density inspection in respect of the next zone of the i-th cigarette rod section. Thereafter, if it is determined at step S23 that the density inspection for the final zone of the i-th cigarette rod portion is completed, without the fault determination in step S22, the i-th cigarette rod portion is determined as having a sufficient density (step S24). The control flow returns to step S11 to await for the start of the density inspection for the next cigarette rod portion.

According to the aforementioned fault determining procedure, those cigarette rod portions for which the possibility of including a local low-density portion is high can be detected reliably accurately with use of a detection logic which is relatively simple, without the need of narrowing the widths of the windows 28, 29 of the radiation type density detector 13 and without impairing the detection, based on the density signal generated by the detector 13, of average density in respect of the entire length of cigarette rod portion.

The present invention is not limited to the foregoing embodiment. For instance, a density detector of another type may be employed in stead of the radiation type density detector 13.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A cigarette density inspection method, comprising the steps of:
   (a) detecting in advance, as a reference density signal, a density signal indicating a density of a reference cigarette which includes a local low-density portion;
   (b) detecting, as an actual density signal, a density signal which indicates a density of an inspected cigarette;
   (c) determining a correlation between a changing pattern of the reference density signal and that of the actual density signal; and
   (d) determining whether the inspected cigarette includes a local low-density portion based on the correlation determined in said step (c).

2. The cigarette density inspection method according to claim 1, wherein the changing pattern of the reference density signal is determined in advance before the actual density signal is detected.

3. The cigarette density inspection method according to claim 1, wherein the inspected cigarette is a cigarette rod which is continuously fed from a wrapping section of a cigarette manufacturing machine for wrapping tobacco shreds by a paper web, and the cigarette rod includes cigarette rod portions respectively corresponding to individual cigarette products into which the cigarette rod is cut after a density inspection is completed.

4. The cigarette density inspection method according to claim 3, wherein said step (a) includes a sub-step of detecting in advance, as the reference density signal, a density signal which indicates a density of a predetermined cigarette zone, including the local low-density portion, of the reference cigarette;

said step (b) includes a sub-step of detecting, as actual density signals, density signals each of which indicates a density of a corresponding one of plural zones of each cigarette rod portion, the plural zones each having the same length as that of the predetermined cigarette zone and partly overlapping an adjacent zone;

said step (c) includes a sub-step of determining nonconformity degree between the changing pattern of the reference density signal and that of each of the actual density signal; and said step (d) determines that the inspected cigarette includes the local low-density portion if any one of the nonconformity degrees determined in said step (c) is less than an allowable limit.

5. The cigarette density inspection method according to claim 4, wherein said step (a) includes a sub-step of sampling the reference density signal at intervals of a predetermined period;

said step (b) includes a sub-step of sampling the actual density signal, at intervals of a period which is the same as the predetermined period, in respect of each of the plural zones of each cigarette rod portion; and said step (c) includes a sub-step of determining a square or an absolute value of a difference between each of the actual density signals sampled in said step (b) and a corresponding one of the reference density signals sampled in said step (a), and a sub-step of determining, as the nonconformity degree, a sum of the squares or the absolute values in respect of all of the actual and reference density signals.

6. The cigarette density inspection method according to claim 4, further comprising the steps of:

(e) determining an average density of each zone of each cigarette rod portion based on the density signals in respect of said zone; and (f) determining that a corresponding one of the cigarette rod portions is fault if it is determined in said step (d) that any one of the nonconformity degrees in respect of the plural zones of the cigarettes rod portion is less than the allowable limit and if any one of the average densities, determined in said step (e) in respect of those zones whose nonconformity degrees are less than the allowable limit, is less than a predetermined average density.

7. The cigarette density inspection method according to claim 1, wherein the step of detecting a density signal indicating a density of a reference cigarette includes the step of detecting said local low-density as having a length which is significantly shorter than an axial length of said reference cigarette.

8. The cigarette density inspection method according to claim 7, wherein the step of detecting said local low-density portion includes the step of detecting a local low-density portion having a length which is approximately equal to a diameter of said reference cigarette.

9. The cigarette density inspection method according to claim 1, wherein the step of detecting a density signal indicating a density of a reference cigarette includes the step of detecting a density profile along an axial length of said reference cigarette, wherein said local low-density portion of said reference cigarette is detected as a decreased-density portion along an axial length of the reference cigarette.

10. The cigarette density inspection method according to claim 1, wherein the step of detecting a density signal which indicates a density of an inspected cigarette includes the step of detecting a density profile along an axial length of said inspected cigarette, said density signal of the inspected cigarette providing an indication of the existence of a local low density portion along an axial length of said inspected cigarette.

11. The cigarette density inspection method according to claim 1, wherein the step of determining a correlation between the changing pattern of the reference density signal and the actual density signal includes the step of determining a degree of nonconformity between the reference and actual density signals, the inspected cigarette being a fault cigarette if the degree of nonconformity is less than an allowable limit.

12. The cigarette density inspection method according to claim 1, wherein the step of determining a correlation between a changing pattern of the reference density signal and the actual density signal includes:

determining a difference between the two signals; and using said difference to obtain a nonconformity degree, wherein the cigarette is determined to be faulty if the nonconformity degree is less than an allowable limit.

13. The cigarette density inspection method according to claim 1, wherein:

the step of detecting a signal indicating a density of the inspected cigarette includes detecting said density using a density detector; and the step of detecting a signal indicating the density of said reference cigarette includes detecting said density using a reference density signal detecting device.

14. The cigarette density inspection method according to claim 13, wherein the step of determining a correlation includes the steps of:

sending the signal indicating a density of an inspected cigarette to an average density calculating section and to a nonconformity degree calculating section; and sending the signal indicating a density of the reference cigarette to said nonconformity degree calculating section.

15. The cigarette density inspection method according to claim 14, wherein the density signals indicating the inspected and reference cigarette densities are compared in the nonconformity degree calculating section, a nonconformity signal being generated in the nonconformity degree calculating section, the correlation step further including:

sending an average density signal to a fault determining section;

sending a signal indicating a degree of nonconformity of the inspected cigarette from the nonconformity degree calculation station to a low density calculation section; and sending a low density signal from the low density calculation station to the fault determining section, wherein the step of determining whether the inspected cigarette includes a low-density portion includes the step of using said average density signal and said low density signal.

16. A cigarette density inspection method, comprising the steps of:

sampling, at intervals of a predetermined period, a density signal of a predetermined cigarette zone of a reference cigarette including a local low-density portion, while translating the reference cigarette in a direction aligned with a longitudinal axis of the reference cigarette;

determining a reference density signal using the sampled reference cigarette density signal, the reference density signal indicating a density of the reference cigarette, the predetermined cigarette zone being shorter in length than the reference cigarette and including an indication of the local low-density portion;

sampling, at intervals having the same length as the predetermined period for the sampling associated with the reference cigarette, a density signal associated with plural zones of an inspected cigarette while translating the inspected cigarette in a direction aligned with a longitudinal axis of the inspected cigarette;

determining an actual density signal indicating a density of the inspected cigarette using the sampled inspected cigarette density signal, the plural zones of an inspected cigarette partially overlapping one another and each having substantially the same length as that of the predetermined cigarette zone in the reference cigarette;

determining a correlation between a changing pattern of the reference density signal in the predetermined cigarette zone of the reference cigarette and a changing pattern of the actual density signal at lengthwise portions of the inspected cigarette, on the basis of a sum of squares or absolute values of differences between actual density signals and reference density signals; and determining whether the inspected cigarette includes a local low-density portion based on the correlation determined in the correlation determination step.

* * * * *